United States Patent
Davies et al.

[11] Patent Number: 6,146,615
[45] Date of Patent: Nov. 14, 2000

[54] CONTRAST AGENTS FOR IMAGE ENHANCEMENT IN MAGNETIC RESONANCE IMAGING

[75] Inventors: Julian A. Davies, Sylvania, Ohio; Wolfgang Ebert; Bernd Raduechel, both of Berlin, Germany

[73] Assignees: The University of Toledo, Toledo, Ohio; Schering Aktiengesellschaft, Germany

[21] Appl. No.: 09/227,962

[22] Filed: Jan. 11, 1999

[51] Int. Cl.$^7$ ................................... A61B 5/055
[52] U.S. Cl. ................ 424/9.36; 424/9.361; 514/182; 514/502; 514/836; 544/64; 544/78; 548/402; 548/523; 556/138; 556/139; 564/82
[58] Field of Search ................ 424/9.361, 9.36; 556/45, 138, 139; 514/492, 502, 836, 184; 544/64, 78; 548/402, 523; 564/82

[56] References Cited

U.S. PATENT DOCUMENTS

| | | |
|---|---|---|
| 4,880,008 | 11/1989 | Lauffer . |
| 5,010,191 | 4/1991 | Engelstad et al. . |
| 5,494,656 | 2/1996 | Davies . |
| 5,622,687 | 4/1997 | Krishnan et al. ............ 424/9.33 |
| 5,786,496 | 7/1998 | O'Halloran et al. .......... 556/137 |
| 5,858,329 | 1/1999 | Peng et al. ............... 424/9.361 |
| 5,869,025 | 2/1999 | Peng et al. ............... 424/9.36 |

OTHER PUBLICATIONS

Badawi et al.,*Pharmazie* 35(12):748–751 (1980).

*Primary Examiner*—Gary E. Hollinden
*Attorney, Agent, or Firm*—MacMillan, Sobanski & Todd, LLC

[57] ABSTRACT

A compound of formula (I):

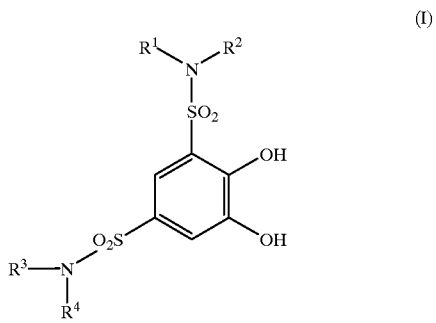

wherein, $R^1$, $R^2$, $R^3$ and $R^4$ are selected independently from hydrogen, alkyl, and alkyl substituted with one or more —O— atoms, or where $R^1$, $R^2$ and $R^3$, $R^4$ are ring residues. The compound is capable of functioning as a ligand and complexing with paramagnetic Fe(III) ion for use as a second-sphere contrast enhancing agent for magnetic resonance imaging of tissue, and a method of administering the second sphere contrast agent.

16 Claims, 3 Drawing Sheets

CONTRAST AGENTS FOR IMAGE ENHANCEMENT IN MAGNETIC RESONANCE IMAGING

FIELD OF THE INVENTION

This invention relates generally to a compound capable of complexing with paramagnetic Fe(III) ion usefull as a contrast agent for image enhancement in magnetic resonance imaging. More particularly, this invention is directed to tissue-specific, second-sphere complexes comprising Fe(III) complexes of catechol-based ligands, and to a method for performing magnetic resonance imaging of a patient using the second-sphere complexes.

BACKGROUND OF THE INVENTINO

Magnetic resonance imaging (MRI) is a nuclear magnetic resonance (NMR) technique that may be used clinically to differentiate between normal and abnormal tissues. The $^1$H NMR imaging method is based upon differences in water proton concentrations and relaxation rates within different tissue types.

When magnetic resonance imaging was first being developed as a diagnostic tool, it was believed that there would be no need for a contrast agent and, that by the use of carefully selected pulse sequences, it would be possible to differentiate tissue types and provide accurate diagnoses. See, Wolf, C. L., Burnett, K. R., Goldstein, U. & Joseph P. M. Magn. Res. Ann. 1985, 231. In many areas of diagnostic medicine this has been found not to be the case, leading to contrast agents being developed.

Contrast agents function in such a way that they lead to the alteration of an image so that, if localized within, say, a tumor, the signal intensity due to the water protons within the tumor becomes different from that of the surrounding tissue. There are two ways in which these alterations can be made. The signal can become brighter or the signal can become darker, and both of these effects are obtainable using various types of contrast agents.

Nearly all of the classes of contrast agent create their desired effect by changing the spin-lattice relaxation time ($T_1$) and/or the spin-spin relaxation time ($T_2$) of the water protons (one notable exception is the family of diamagnetic fluorocarbons, which finction by replacing water, thus leading to a null signal for that region). See, Wood, M. L. & H. P.A.J. Mag. Reson. Imag. 1993, 3, 149. See, Lauffer, R. B. Invest. Radiol. 1990, 25, S32. Those contrast agents that operate predominantly on spin-spin relaxation times are the superparamagnets, such as particulate iron oxides. Those contrast agents that operate predominantly on the spin-lattice relaxation time are the paramagnets. These species possess unpaired electrons and thus have a net magnetic moment. It is this magnetic moment which leads to an increase in the spin-lattice relaxation rate of water protons, as the magnetic moment stimulates the transition from a high-energy spin state to a lower energy spin state. For contrast-enhanced MR imaging it is desirable to have a large magnetic moment, with a relatively long electronic relaxation time. Based upon these criteria, candidates for use in contrast agents include Gd(III), an $f^7$ system, and the $d^5$ systems Mn(H) and high-spin Fe(III). Gadolinium(III) has the largest magnetic moment among these three and it has been extensively studied.

It might seem that the aqua ion of each of these paramagnetic metals would be a good choice for use as a contrast agent, as these have the largest possible number of bound water molecules. However, the aqua ions are relatively toxic, and there exists little opportunity to control the biodistribution of these species. The reported $LD_{50}$ values for the metal chloride salts in aqueous solution are 1.4, 1.5 and 1.6 mmol/kg for gadolinium, manganese and iron respectively when administered to mice i.p. See, Lauffer, R. B. Chem. Rev. 1987, 87, 901.

In attempts to solve both of these problems, a variety of ligands—organic molecules which are able to coordinate to the metal ions—have been employed. For current clinical contrast agents that are based on gadolinium, ligands are employed which occupy almost all of the coordination sites on the metal ion, typically leaving one site available for water molecules to reversibly bind. This approach reduces the toxicity of the metal ion and, by careful variation of the ligand system, potentially allows control of the biodistribution such that in vivo targeting may be achieved. Other desirable properties of a potential contrast agent may include prompt clearance of an extracellular agent as well as in vivo and in vitro stability.

It will be appreciated that there are potential advantages with the use of manganese and iron in comparison to gadolinium because both iron and manganese have a natural human biochemistry which may make it simpler to design target-specific contrast agents based on known biochemical uptake mechanisms, i.e., tissue specificity.

Another problem to overcome is the choice of ligand system. More particularly, it is desirable to provide a ligand system that will reduce the toxicity to an acceptable level, and give the in vivo desired targeting.

It will be appreciated from the foregoing that there is still a significant need for a tissue-specific contrast agent for image enhancement in magnetic resonance imaging that addresses at least some of the problems of the prior art. It is another object of the present invention to provide a tissue-specific contrast agent for image enhancement in magnetic resonance imaging having toxicity levels no greater than clinical agents currently used, e.g., Gd-DTPA (gadolinium ion chelated with the ligand diethylenetriaminepentaacetic acid). Yet another object of the present invention is to provide a tissue-specific contrast agent for image enhancement of tumors. Still another object of the present invention is to provide a tissue-specific contrast agent for image enhancement of tumors, necrotic tissue and/or necrotic tumor tissue. Another object of the present invention is to provide a tissue-specific contrast agent for image enhancement to provide precise localization and sizing of the tissue.

SUMMARY OF THE INVENTION

Briefly, in accordance with the present invention, there is provided a compound of formula (I):

wherein, $R^1$, $R^2$, $R^3$ and $R^4$ are selected independently from hydrogen, alkyl, and alkyl substituted with one or more —O— atoms, or where $R^1$, $R^2$ and $R^3$, $R^4$ are ring residues. The compound is capable of functioning as a ligand and complexing with paramagnetic Fe(III) ion for use as a second-sphere contrast enhancing agent for magnetic resonance imaging of tissue, and a method of administering the second-sphere contrast agent.

Also contemplated by the present invention is a method for magnetic resonance image enhancement utilizing the contrast agents.

BRIEF DESCRIPTION OF THE DRAWINGS

Further features and other objects and advantages of this invention will become clear from the following detailed description made with reference to the drawings in which.

DETAILED DESCRIPTION OF THE PREFERRED EMBODIMENT

The development of pharmaceutical agents which enhance image contrast between tissue types presents unique challenges since such agents are not themselves imaged but rather function through affecting water molecule proton relaxation rates. This important distinction between image contrast agents and other types of clinically useful diagnostic pharmaceuticals, such as for example X-ray contrast agents or radiopharmaceuticals, leads to major differences in the in vivo distribution requirements of each type of agent. Thus, for a magnetic resonance imaging contrast agent to be effective, it is required that the water proton relaxation rate in the target tissue be affected differently from the relaxation rate of the water protons in the surrounding tissue. Such differentiation is possible because of the mode of action of these image enhancement agents. Paramagnetic species, such as certain complexes of metal ions, can alter the longitudinal and/or transverse relaxation rates of adjacent nuclei by dipolar interactions.

The present invention is directed to a tissue-specific class of magnetic resonance imaging contrast agents displaying important properties in medical diagnosis. More particularly, the present invention is directed to a class of magnetic resonance imaging contrast agents that accumulates in tissue, such as tumor tissue, necrotic tissue and/or necrotic tumor tissue. For example, an important aspect of the contrast agents in accordance with the present invention is that they have been found to accumulate in necrotic tumor tissue, necrotic kidney tissue and ischemic myocardium.

The class of magnetic resonance imaging contrast agents comprises a complex of paramagnetic ions chelated with catecholate ligands of formula (I):

wherein, $R^1$, $R^2$, $R^3$ and $R^4$ are selected independently from hydrogen, alkyl, and alkyl substituted with one or more —O— atoms, or where $R^1$, $R^2$ and $R^3$, $R^4$ are ring residues.

The metal ion with the most suitable magnetic moment and relaxation efficiency for this purpose is Fe(III). In order for the Fe(III) metal ion to enhance the relaxation rate of water protons in tissue, it is important that the water molecules approach close to the paramagnetic center.

It is believed that three basic types of interactions between the metal ion and water molecules may occur. In an inner-sphere interaction, water molecules bind to and exchange with the metal ion, for a very effective contact. In an outer-sphere interaction, all of the Fe(III) metal ion coordination sites are occupied by a set of ligands, and so water molecules are affected only through translational diffusion past the paramagnetic center. In an intermediate case, i.e., second-sphere interaction, the Fe(III) metal ion is surrounded by a set of ligands which prevent direct coordination of water molecules to the metal ion. However, the ligands of a second-sphere complex also provide bonding sites for the hydrogen bonding of water molecules thereto.

Fe(III) metal ions which interact with water molecules by an inner-sphere mechanism are very effective for enhancing relaxation rates, but such ions generally exhibit very high toxicities. The origin of this toxicity may lie in the availability of coordination sites at the Fe(III) metal ion center which leads to binding by not only water molecules but also by activated oxygen, nitrogen, or sulfir groups of a number of biomolecules. The coordination sites at the metal center can essentially be removed by using a suitable set of ligands. However, although this reduces toxicity, it typically leaves only the less-effective, outer-sphere interactions with water molecules to provide relaxation rate enhancement. To balance these effects, the complexes in accordance with the present invention are designed to operate primarily by second-sphere interactions and have been developed for use in magnetic resonance imaging.

The ligands useful for second-sphere relaxation enhancement must meet specific requirements. They must bind strongly to paramagnetic Fe(III) ions, since ligand dissociation would result in metal ion toxicity and ligand-derived organic toxicity. Useful ligands must form complexes which are excreted efficiently to prevent long-term toxicity by, for example, the accumulation in lipophilic membranes or retention by cells in the reticular endothelial system. Moreover, the useful ligands must provide sites for the hydrogen bonding of water molecules.

In accordance with the present invention the catecholate ligands are of formula (I):

(I)

wherein, $R^1$, $R^2$, $R^3$ and $R^4$ are selected independently from hydrogen, alkyl, and alkyl substituted with one or more —O— atoms, or where $R^1$, $R^2$ and $R^3$, $R^4$ are ring residues.

Preferred embodiments of the catecholate ligands are of formulas (II)–(XXII).

(II)

(III)

(IV)

(V)

(VI)

(VII)

(VIII)

(IX)

(XX)

(XXI)

(XXII)

The mechanism of efficient excretion of the Fe(III) metal ion complexes from the body, which preferably should occur within a few hours following administration, is less-well understood. Only certain broad principles are available to assist in the complex design. Thus, the presence of highly charged and/or hydrogen bonding groups and the absence of lipophiiic side chains minimizes interactions with membranes, plasma proteins, etc., and so allows for effective renal excretion. Certain anionic complexes are excreted by the hepatobiliary pathway in competition with excretion via the kidneys. Although poorly understood, excretion via the liver may involve transport of anionic complexes by the same agents that transport fatty acids, bile acids, and heme degradation products. Thus, for efficient excretion to avoid long-term toxicity, the factors promoting both renal and hepatobiliary pathways must be maximized.

The presence of hydrogen bonded water molecules is required for the operability and utility of second-sphere contrast agents complexes, according to the present invention. Complexes that fall into this group rely primarily on the hydrogen bonding of water molecules to the heteroatoms that form the paramagnetic Fe(III) metal ion-to-ligand linkages.

The second-sphere complexes of the present invention comply with the requirements set forth above. The inventive complexes are prepared utilizing paramagnetic Fe(III) metal ions, which are detectable in their chelated form by magnetic resonance imaging.

Suitable ligands for preparing the second-sphere complexes according to the present invention include catechol-based ligands where the ligands are of the general formula (I):

wherein, $R^1$, $R_2$, $R^3$ and $R^4$ are selected independently from hydrogen, alkyl, and all substituted with one or more —O— atoms, or where $R^1$, $R^2$ and $R^3$, $R^4$ are ring residues. The pendant sulfonamide groups may act as additional hydrogen bonding sites for water molecules.

The Fe(III) complexes of the compound where $R''(n=1, 2, 3$ or $4)$ is ethyl for example, displays the unexpected property of accumulation in necrotic tumor tissue and in necrotic kidney tissue.

The second-sphere complexes of the present invention may be administered in any convenient manner to the subject. For example, the complexes may be dissolved in a saline solution and injected intravenously or subcutaneously. Generally, the dosages will be limited to only those amounts necessary and sufficient to allow detection by magnetic resonance imaging. Such dosages typically range from about 0.02 mmol/kg to about 0.5 mmol/kg. Preferably, the dosages range from about 0.05 mmol/kg to about 0.15 mmol/kg.

The second-sphere complexes of the present invention enhance magnetic resonance imaging conducted utilizing conventional nuclear magnetic resonance devices. The complexes shorten the imaging time required to produce and maintain images of the target tissues.

The invention will be further clarified by a consideration of the following examples, which are intended to be purely exemplary of the invention.

LIGAND SYNTHESIS

Chlorosulfonic acid (35 mL) was placed in a 100-mL round-bottomed flask and, under nitrogen, was heated to 110° C. To this, catechol (4.99 g) was added giving a purple solution with evolution of hydrogen chloride. The temperature was maintained at 110° C. for 1.5 hours. After this time, the reaction mixture was cooled to below 0° C. and concentrated hydrochloric acid (35 mL) slowly was added under nitrogen. A brown solid formed and diethyl ether (100 mL) was added under nitrogen. Further addition of diethyl ether allowed separation of an aqueous phase which was washed with diethyl ether (5×100 mL). The diethyl ether fractions were separated and combined, and this yellow solution was added to diethylamine (50 mL) dropwise under nitrogen with cooling in an ice bath. The resulting green solution was stirred for 2 hours. The diethyl ether was then removed on a rotatory evaporator and the resulting oil was acidified with hydrochloric acid to give a brown solution. The solution was extracted with methylene chloride (5×100 mL) to produce a dark brown methylene chloride solution. The methylene chloride was removed on a rotatory evaporator to leave a black oil. Repeated extraction with boiling hexanes followed by cooling and filtration of the hexanes resulted in isolation of a white solid. Proton NMR ($D_2O$): signals at 7.59 (d, 1H), 7.46 (d, 1H), 3.31 (q, 4H), 3.23 (q, 4H), 1.17 (t, 6H), 1.14 (t, 6H) parts per million. $^{13}C\{^1H\}$ NMR ($D_2O$): signals at 146.37, 145.56, 132.86, 123.57, 118.05, 116.76, 42.29, 42.15, 14.16, 13.91 parts per million. Ligand XI was formed.

Other ligands, e.g., ligands II–XXI were synthesized by similar methods. X-ray crystal structures of selected ligands X and XVII confirmed the structural assignments made. Other data from NMR, mass spectroscopy and elemental analysis confirmed the structural assignments made for the remaining ligands.

SYNTHESIS OF IRON(III) COMPLEXES

Iron(III) complexes for MR imaging experiments were prepared in two different ways:

1. Fe(III) solutions were prepared by dissolution of $FeCl_3$ in a small amount of distilled, deionized water with the amounts necessary of the appropriate ligand. The pH was adjusted to 7.2 with aqueous sodium hydroxide and/or hydrochloric acid. The volumes were adjusted with distilled, deionized water to give the desired concentrations for imaging experiments.

2. Fe(III) complexes were isolated as solid materials by reaction of Fe(III) tris(acetylacetonate) with three molar equivalents of ligand in water containing three molar equivalents of NaOH at 80° C. Extraction with diethyl ether and/or methylene chloride to remove acetylacetone was followed by lyophilization to produce solid compounds. Molecular formulas were confirmed by elemental analysis. Solid compounds were dissolved in water to generate aqueous solutions for administration.

MR IMAGING EXPERIMENTS ON HEALTHY RATS

Animal studies were performed with a 1.5-T superconducting MR unit (Signa. GE Medical Systems) using a send-and-receive head coil containing two anesthetized female Fischer 344 rats. After a localizer image were obtained, a spin-echo pulse sequence were used with a 256×256 matrix (three signals acquired) over a 20-cm field of view with a thickness of 3 mm and a 1.5-mm intersection gap. The pulse sequence parameters were $T_R=300$ ms and $T_E=20$ ms. Sagittal images were collected before administration of the contrast agent, and after administration, five more images were collected. Operator defined region-of-interest (ROI) measurements were made upon the organs under study for the pre- and postcontrast images. ROI measurements were recorded for the liver and kidney. For the liver, three slices were studied and for the kidneys, a single slice through each kidney was studied.

Percent enhancement was calculated by the following equation:

$$\% \text{ Enhancement} = \frac{\text{Post value} - \text{Pre-value}}{\text{Pre-value}} \times 100$$

Female Fischer 334 rats were used in the imaging experiments. The subjects were weighed and anesthetized with 65 mg/kg pentobarbital. The preinjection pulse sequence was performed, then the contrast agent was administered. The concentration used was 0.10 mmol/kg with an injection volume of 0.5 mL used throughout, administered over a time range of approximately three minutes. The contrast agent was injected into the tail vein via a 27-gauge butterfly needle, followed by a 1-mL saline flush. After administration of the contrast agent the spin-echo pulse sequences were performed. Two subjects were studied for each contrast agent.

TISSUE-SPECIFICITY: LIVER SPECIFICITY OF THE TRIS(LIGAND)IRON(III) COMPLEX OF LIGAND XI

Figure 1:
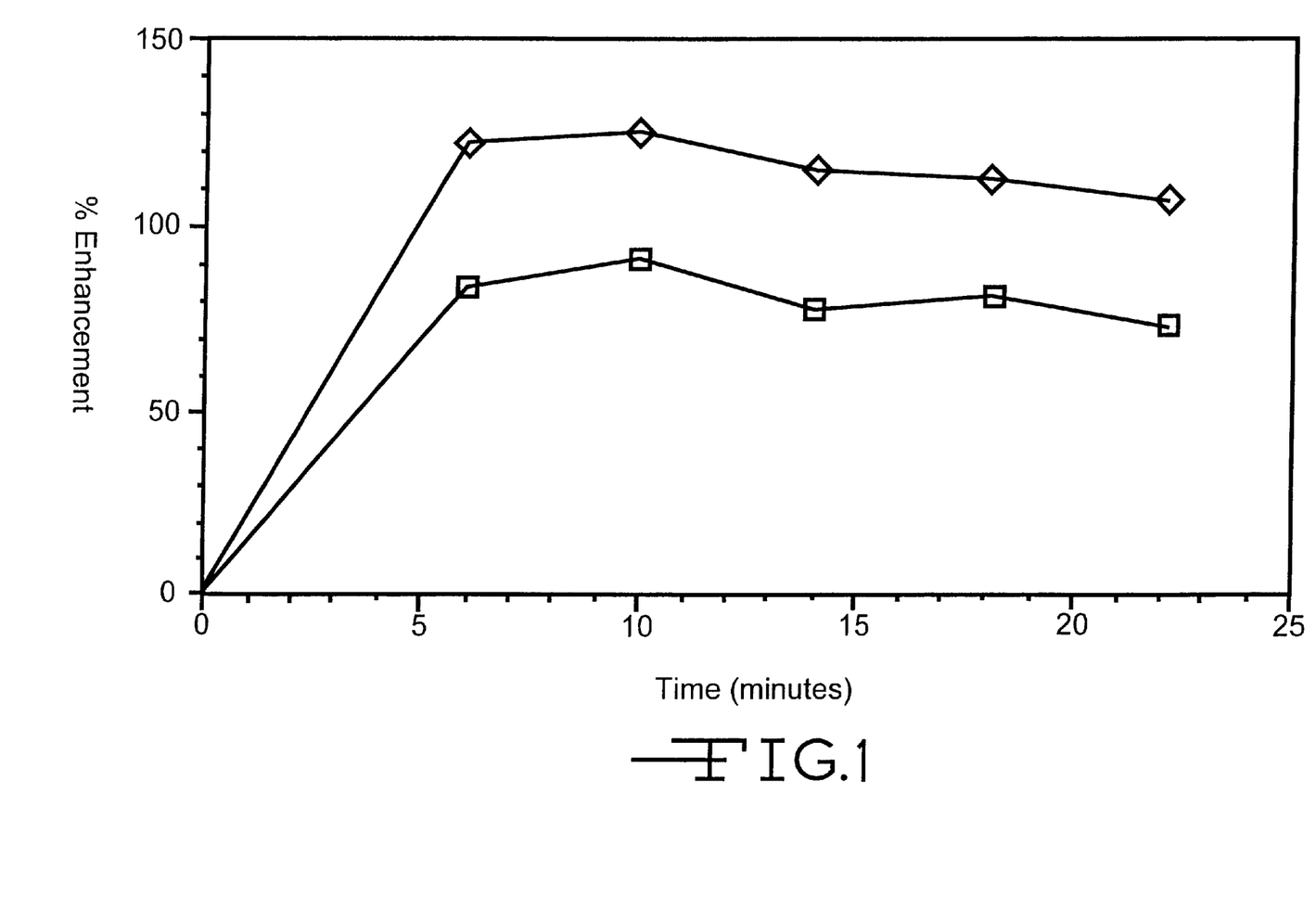
FIG. 1 is a plot of percent enhancement of the liver and kidney of a rat versus time after injection of the contrast agent.

FIG. 1 is a plot of percent enhancement of the liver and kidneys of a rat injected with the Fe(III) complex of ligand XI and it shows enhancement kinetics for the liver and kidney. The example compound shows significant liver-specificity.

To illustrate the liver-specificity of the example compound, the enhancement kinetics shown in FIG. 1 was compared with that of a compound which does not show this tissue specificity, e.g., Fe(III) tris(tironate), See Davies et al.; Academic Radiology 1996, 3, 936–945; U.S. Pat. No. 5,494, 656, where liver enhancements of no greater than 15% were obtained over the same time period.

MR IMAGING EXPERIMENTS ON TUMOR-BEARING RATS: EXAMPLE OF TISSUE-SPECIFICITY: TUMOR AND TUMOR-NECROSIS SPECIFICITY OF THE TRIS (LIGAND)IRON(III) COMPLEX OF LIGAND XI

A $T_1$-weighted MRI examination (SE 400/15; SISCO SIS 85, 2 T) of the iron complex of ligand XI, Fe-DESAC, in rats (inbred Copenhagen, male, ca. 250 g bw) with implanted prostatic tumors (Dunning R3327, MAT/Lu) in the thigh muscles has been performed. The results are striking when compared with those obtained with Gd-DTPA and showed that Fe-DESAC gives rise to sustained enhancement specifically of necrotic tumor tissue at 24 hr post contrast. No such enhancement was found with vital tumors and no such enhancement was found with Gd-DTPA.

After a single iv application of Fe-DESAC or Gd-DTPA, significant tumor enhancement 1 hr post contrast (see Table 1) and 3 hr post contrast (see Table 1), respectively, was found. Thus, differentiation of tumor from surrounding muscle was straightforward with both contrast agents.

Twenty four hours post contrast, Gd-DTPA gave no significant enhancement of tumor (see Table 1), whereas the Fe(III) complex Fe-DESAC was found to give sustained positive enhancement of a large (almost completely necrotic) tumor (see Table 1) but no significant enhancement of a small (almost completely viable) tumor (see Table 1).

TABLE 1

Percentage enhancement after 100 μmol agent/kg bw iv.

| Compound | Fe-DESAC | | Gd-DTPA | |
|---|---|---|---|---|
| Time post contrast | 1 hr | 24 hr | 1 hr | 24 hr |
| Small, non-necrotic tumor | +93 ± 28 | +23 ± 34 | n.d. | n.d. |
| Muscle | +31 ± 16 | +6 ± 13 | n.d. | n.d. |

TABLE 1-continued

Percentage enhancement after 100 μmol agent/kg bw iv.

| Compound | Fe-DESAC | | Gd-DTPA | |
|---|---|---|---|---|
| Time post contrast | 1 hr | 24 hr | 1 hr | 24 hr |
| Large, necrotic tumor | +85 ± 8 | +66 ± 0 | +52 ± 14 | −11 ± 8 |
| Muscle | +30 ± 10 | +8 ± 10 | +10 ± 6 | −4 ± 2 |

MR images showed sustained positive enhancement of a large (almost completely necrotic) tumor at 24 hr post contrast. MR images also showed the absence of positive enhancement of a small (almost completely viable) tumor at 24 hr post contrast. Thus, Fe-DESAC allowed assessment of tumor necrosis and differentiation from viable tumor through measurement both 1 hr and 24 hr post contrast.

EXAMPLES OF TISSUE-SPECIFICITY: TUMOR SPECIFICITY OF THE TRIS(LIGAND)IRON(III) COMPLEXES OF: LIGANDS XI, XVII AND XXII

A $T_1$-weighted MRI examination (SE 400/15; SISCO SIS 85, 2 T) of three of these new MR contrast agents, the Fe(III) complexes of ligands XI, XVII and XXII in rats (inbred Copenhagen, male, ca. 250 g bw) with implanted prostatic tumors (Dunning R3327, MAT/Lu) in the thigh muscles was performed.

Figure 2:
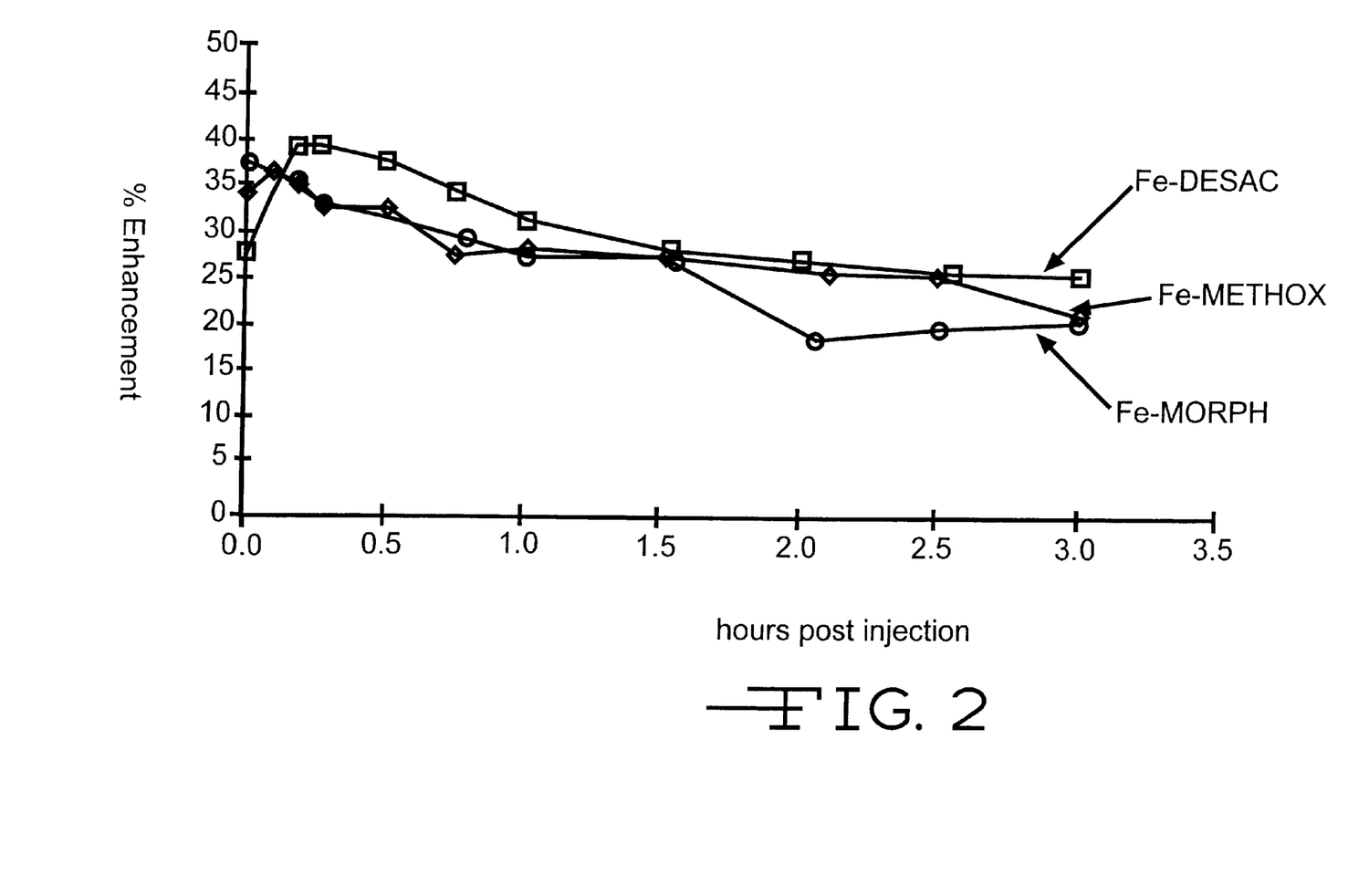
FIGS. 2 and 3 are plots of percent enhancement of muscle tissue and tumors in rats versus time after injection for three different contrast agents.
Figure 3:
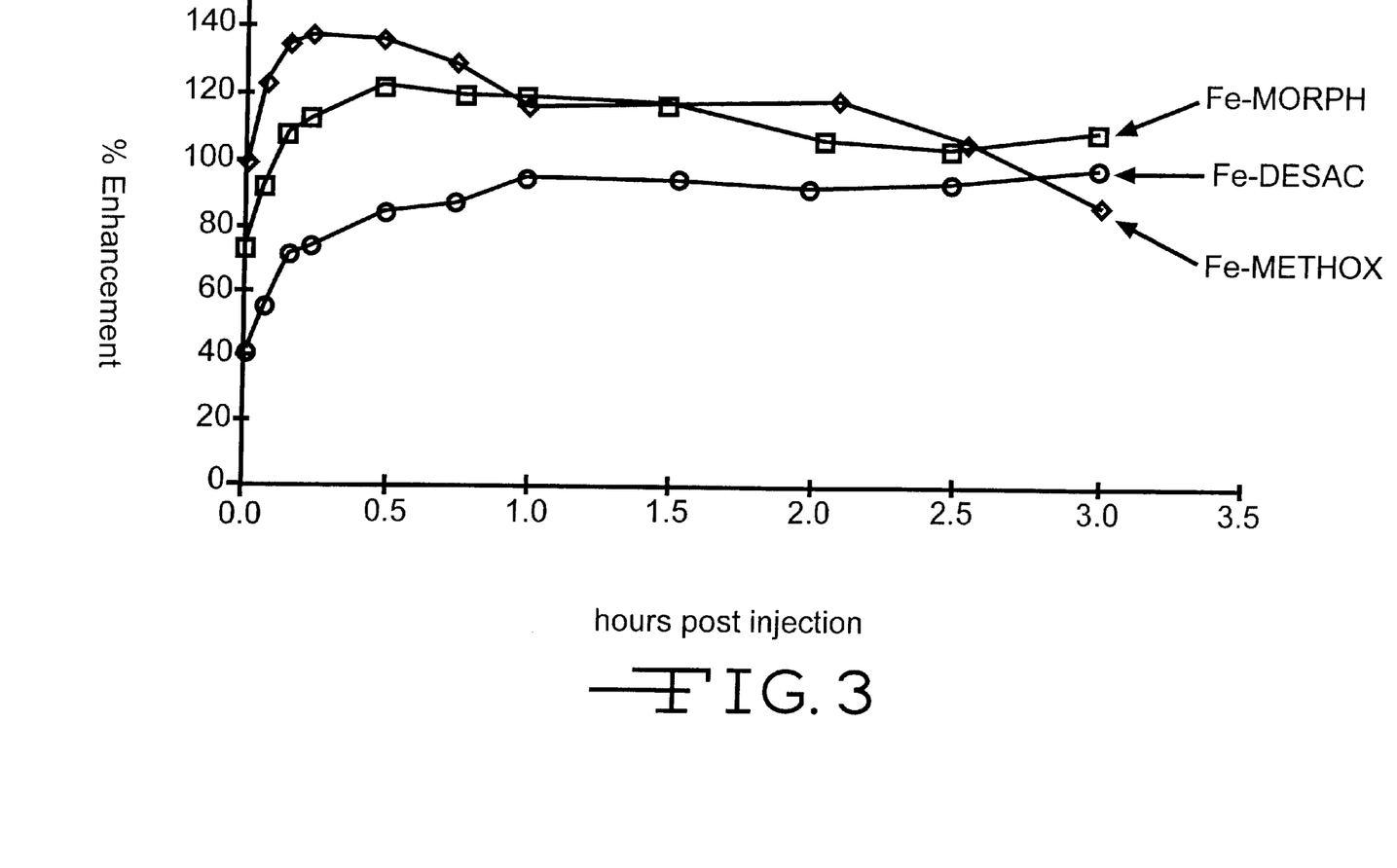

FIGS. 2 and 3 show enhancement of tumor compared to enhancement of muscle (SE 400/15; SISCO SIS 85, 2 T). In these figures, data for the Fe(III) tris(ligand) complex of ligand XI are labelled Fe-DESAC; data for the Fe(III) tris(ligand) complex of ligand XVII are labelled Fe-METHOX; data for the Fe(III) tris(ligand) complex of ligand XXII are labelled Fe-MORPH. These data show that the Fe(III) complexes gave rise to prolonged enhancement of tumor tissue over muscle. In addition, the foregoing complexes were compared to Gd-DTPA in muscle and tumor tissue whereby the complexes including ligands XI, XVII or XXII exhibited superior enhancement to that obtained with Gd-DTPA.

At least one of the foregoing tests described above was performed with one or more complexes of Fe(III) and ligands II–X, XII–XVI and XVIII–XX. The foregoing complexes performed as contrast agents and exhibited tissue specificity superior to that of Gd-DTPA.

The documents, patents and patent applications referred to herein are hereby incorporated by reference.

Having described presently preferred embodiments of the invention, it is to be understood that it may be otherwise embodied within the scope of the appended claims.

What is claimed is:

1. A compound of formula (I) comprising:

wherein, $R^1$, $R^2$, $R^3$ and $R^4$ are selected independently from hydrogen, alkyl, and alkyl substituted with one or more —O— atoms, or where $R^1$, $R^2$ and $R^3$, $R^4$ are ring residues.

2. A compound capable of complexing with a paramagnetic Fe(III) ion, the compound independently selected from:

(XIV)

(XV)

(XVI)

(XVII)

(XVIII)

(XIX)

(XX)

(XXI)

(XXII)

3. A ligand for complexing with paramagnetic FE(III) ion for use as a second-sphere contrast enhancing agent for magnetic resonance imaging of tissue, the ligand of formula (I) comprising:

(I)

wherein, $R^1$, $R^2$, $R^3$ and $R^4$ are selected independently from hydrogen, alkyl, and alkyl substituted with one or more —O— atoms, or where $R^1$, $R^2$ and $R^3$, $R^4$ are ring residues.

4. The second-sphere contrast enhancing agent of claim 3 wherein the tissue is tumor tissue.

5. The second-sphere contrast enhancing agent of claim 3 wherein the tissue is necrotic tissue.

6. The second-sphere contrast enhancing agent of claim 3 wherein the tissue is necrotic tumor tissue.

7. A second-sphere contrast enhancing agent for magnetic resonance imaging of tissue comprising a paramagnetic Fe(III) ion complexed with a ligand independently selected from:

(II)

(III)

(IV)

(V)

(VI)

(VII)

(VIII)

(IX)

-continued (XX)

(XXI)

(XXII)

8. A method for magnetic resonance imaging of tissue in a patient comprising administering an amount of a second-sphere contrast enhancing agent, comprising a paramagnetic Fe(III) ion complexed with ligands of formula (I), where the complex is of the type $[FeL_3]^{3-}$:

(I)

wherein, $R^1$, $R^2$, $R^3$ and $R^4$ are selected independently from hydrogen, alkyl, and alkyl substituted with one or more —O— atoms, or where $R^1$, $R^2$ and $R^3$, $R^4$ are ring residues effective to enhance the magnetic resonance image of the tissue, and obtaining magnetic resonance images of the tissue.

9. The method of claim 8 wherein the tissue comprises tumor tissue.

10. The method of claim 8 wherein the tissue comprises necrotic tissue.

11. The method of claim 8 wherein the tissue comprises necrotic tumor tissue.

12. The method of claim 8 wherein the second-sphere contrast enhancing agent is administered intravenously.

13. A method for performing magnetic resonance imaging of tissue in a patient, comprising:

a) providing a second-sphere contrast enhancing agent, comprising a paramagnetic Fe(III) ion complexed with a ligand of formula (I):

(I)

wherein, $R^1$, $R^2$, $R^3$ and $R^4$ are selected independently from hydrogen, alkyl, and alkyl substituted with one or more —O— atoms, or where $R^1$, $R^2$ and $R^3$, $R^4$ are ring residues;

b) administering the second-sphere contrast enhancing agent to the patient to enhance the nuclear magnetic resonance image of the tissue; and c) subjecting the patient to nuclear magnetic resonance imaging.

14. The method of claim 13 wherein the tissue comprises tumor tissue.

15. The method of claim 13 wherein the tissue comprises necrotic tissue.

16. The method of claim 13 wherein the tissue comprises necrotic tumor tissue.

* * * * *